(12) United States Patent
Dombrowski et al.

(10) Patent No.: US 6,245,806 B1
(45) Date of Patent: Jun. 12, 2001

(54) HIV INTEGRASE INHIBITORS

(75) Inventors: Anne Dombrowski, East Brunswick; Sheo Singh, Edison; Deborah L. Zink, Manalapan, all of NJ (US); Ana Teran; Fernando Pelaez, both of Madrid (ES); Daria Hazuda, Doylestown, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/625,246

(22) Filed: Jul. 25, 2000

Related U.S. Application Data

(60) Provisional application No. 60/146,994, filed on Aug. 3, 1999.

(51) Int. Cl.[7] .................................................. A61K 31/335
(52) U.S. Cl. .......................... 514/450; 549/354; 549/358
(58) Field of Search ................................... 549/354, 358; 514/450

(56) References Cited

PUBLICATIONS

L. Ratner et al., "Complete Nucleotide sequence of the AIDS virus, HTLV–III", Nature, vol. 313, pp. 277–284 (Jan. 24, 1985).

H. Toh et al., "Close structural resemblance between putative polymerase of a Drosophila transposable genetic element 17.6 and pol gene product of Moloney murine leukaemia virus", The EMBO Journal, vol. 4, No. 5, pp. 1267–1272 (1985).

M. D. Power et al., "Nucleotide Sequence of SRV–1, Type D Simian Acquired Immune Deficiency Syndrome Retrovirus", Science, vol. 231, pp. 1567–1572 (1986).

L. H. Pearl et al., "A structural model for the retroviral proteases", Nature, vol. 329, pp. 351–354 (Sep. 24, 1987).

H. Zhao et al., "Hydrazide–Containing Inhibitors of HIV–1 Integrase" J. Med. Chem., vol. 40, pp. 937–941 (1997).

R. L. LaFemina et al., "Inhibition of Human Immunodeficiency Virus Integrase by Bis–Catechols" Antimicrobial Agents & Chemotherapy, vol. 39, No. 2, pp. 320–324 (Feb. 1995).

*Primary Examiner*—Amelia Owens
(74) *Attorney, Agent, or Firm*—Kenneth R. Walton; Melvin Winokur

(57) ABSTRACT

Novel tetracyclic aromatic ketones are natural product compounds useful in the inhibition of HIV integrase, the prevention or treatment of infection by HIV and the treatment of AIDS, either as compounds, pharmaceutically acceptable salts, pharmaceutical composition ingredients, whether or not in combination with other antivirals, immunomodulators, antibiotics or vaccines. Methods of treating AIDS and methods of preventing or treating infection by HIV are also described. Further, the novel fungal cultures MF6388 (ATCC 74478), Sterile Fungus, and MF6591 (ATCC 74477), Ascochyta sp. are also disclosed. Further, the cultures Sterile Fungus MF6388 (ATCC 74478) and Ascochyta sp. MF6591 (ATCC 74477) are also disclosed, as well as processes for making compounds of the present invention employing the cultures.

12 Claims, No Drawings

HIV INTEGRASE INHIBITORS

This application claims the benefit of U.S. Provisional Application No. 60/146,994, filed Aug. 3, 1999, the disclosure of which is hereby incorporated by reference in its entirety.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, e.g., azidothymidine or AZT. Applicants demonstrate that the compounds of this invention are inhibitors of HIV integrase. The applicants additionally demonstrate that inhibition of integrase in vitro is a direct result of inhibiting the strand transfer reaction catalyzed by the recombinant integrase in vitro. The particular advantage of the present invention is highly specific inhibition of HIV integrase and HIV replication. The compounds of the present invention inhibit integrases of closely related lentiviruses such as HIV 2 and SIV, but not integrases from more distantly related retroviruses, for example RSV. These compounds do not inhibit binding or catalysis of other nucleic acid binding proteins, including enzymatic reactions such as those catalyzed by HIV reverse transcriptase, HIV Rnase H, Influenza transcriptase, Hepatitis C polymerase, Yeast DNA polymerase, DNase I, Eco RI endonuclease, or mammalian polymerase II.

Zhao et al., (J. Med Chem. vol. 40, pp. 937–941 and 1186–1194 (1997)) describe hydrazide and arylamide HIV integrase inhibitors. Bis-catechols useful for inhibiting HIV integrase are described in LaFemina et al. (Antimicrobial Agents & Chemotherapy, vol. 39, no. 2, pp. 320–324, February 1995).

Applicants have discovered that certain tetracyclic aromatic ketones are potent inhibitors of HIV integrase. These compounds are useful for the treatment of AIDS or HIV infections.

BRIEF DESCRIPTION OF THE INVENTION

Compounds of Formula I, as herein defined, are disclosed. These compounds are useful in the inhibition of HIV integrase, the prevention of infection by HIV, the treatment of infection by HIV and in the treatment of AIDS and/or ARC, either as compounds, pharmaceutically acceptable salts or hydrates (when appropriate), pharmaceutical composition ingredients, whether or not in combination with other antivirals, anti-infectives, immunomodulators, antibiotics or vaccines. Methods of treating AIDS, methods of preventing infection by HIV, and methods of treating infection by HIV are also disclosed. Further, the cultures Sterile Fungus MF6388 (ATCC 74478) and Ascochyta sp. MF6591 (ATCC 74477) are also disclosed, as well as processes for making compounds of the present invention employing the cultures.

DETAILED DESCRIPTION OF THE INVENTION

This invention is concerned with compounds of Formula I, combinations thereof, or pharmaceutically acceptable salts thereof, in the inhibition of HIV integrase, the prevention or treatment of infection by HIV and in the treatment of the resulting acquired immune deficiency syndrome (AIDS). Compounds of Formula I are defined as follows:

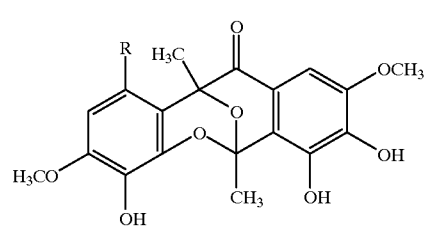

(I)

wherein:
R is selected from:
(a) —CH$_2$OH, and
(b) —CH(=O);
or a pharmaceutically acceptable salt thereof.

Particular compounds of structural Formula I include:

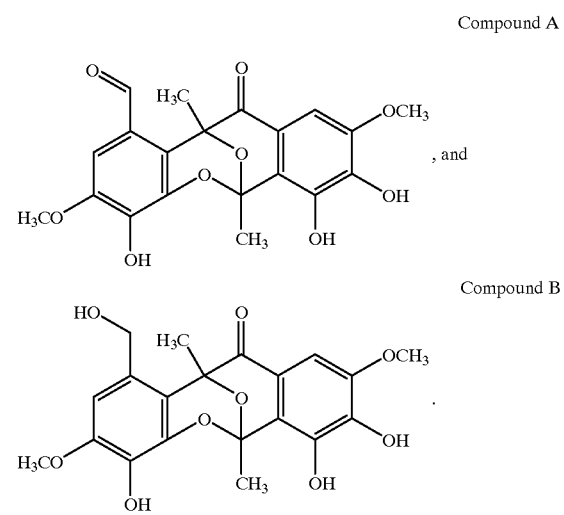

Also included within the present invention are pharmaceutical compositions useful for inhibiting HIV integrase, comprising an effective amount of a compound of this invention, and a pharmaceutically acceptable carrier. Pharmaceutical compositions useful for treating infection by HIV, or for treating AIDS or ARC, are also encompassed by the present invention, as well as a method of inhibiting HIV integrase, and a method of treating infection by HIV, or of treating AIDS or ARC. Additionally, the present invention is directed to a pharmaceutical composition comprising a therapeutically effective amount of a compound of the present invention in combination with a therapeutically effective amount of an AIDS treatment agent selected from:

(1) an AIDS antiviral agent, (2) an anti-infective agent, and (3) an immunomodulator.

The compounds of the present invention may have asymmetric centers and may occur, except when specifically noted, as mixtures of stereoisomers or as individual diastereomers, or enantiomers, with all isomeric forms being included in the present invention.

This invention also discloses the culture MP6388 (ATCC 74478) identified as Sterile Fungus. A culture of MF6388 (ATCC 74478) is defined as substantially free of its natural soil contaminants and capable of forming a compound of Formula (I) in a recoverable amount. The culture should be free from viable contaminating microorganisms deleterious to the production of a compound of Formula (I). A biologically pure culture of MF6388 (ATCC 74478) may also be employed. In one embodiment, the present invention includes a culture of MF6388 (optionally biologically pure), or a mutant thereof, capable of producing in a recoverable amount a compound of Formula (I).

Suitable mutant strains of MF6388 can be obtained by chemically induced mutagenesis using mutagens such as nitrosoguanidine, 1-methyl-3-nitro-1-nitrosoguanidine, ethyl methane sulfonate, 2-aminopurine, and the like. Mutant strains can also be obtained by radiation-induced mutagenesis, such as by irradiation with ultraviolet light (e.g., using a germicidal lamp), X-rays, or gamma rays (e.g., using a cobalt-60 source). Recombinant DNA techniques such as protoplast fusion, plasmid incorporation, gene transfer and the like may also be employed. Further description of mutagenic technqiues can be found in Vinci and Bing, "Strain Improvement by Nonrecombinant Methods", in *Manual of Industrial Microbiology and Biotechnology* 1999, 2d edition, edited by Demain et al., ASM Press, 103–113; and in Carlton and Brown, "Gene Mutation", Chapter 13 in *Manual of Methods for General Bacteriology* 1985, edited by Gerhardt et al., ASM Press, 222–229.

In addition, compounds of the present invention may be prepared by fermentation of the culture MF6388, ATCC 74478.

The present invention also relates to the preparation of compounds of structural Formula I comprising:

(a) fermenting a culture of MF6388 (ATCC 74478), Sterile Fungus or a mutant thereof to produce a fermentation broth, (b) extracting the fermentation broth with an organic solvent, (c) isolating the compounds of structural Formula I.

The compounds of structural Formula I are preferably isolated by partitioning the fermentation extract between the organic solvent and water, followed by size exclusion chromatography and normal or reverse-phase chromatography.

This invention also discloses the culture MF6591 (ATCC 74477) identified as Ascochyta sp. A culture of MF6591 (ATCC 74477) is defined as substantially free of its natural soil contaminants and capable of forming a compound of Formula (I) in a recoverable amount. The culture should be free from viable contaminating microorganisms deleterious to the production of a compound of Formula (I). A biologically pure culture of MF6591 (ATCC 74477) may also be employed. In one embodiment, the present invention includes a culture of MF6591 (optionally biologically pure), or a mutant thereof, capable of producing in a recoverable amount a compound of Formula (I). Suitable mutant strains of MF6591 can be obtained using the methods disclosed above for obtaining mutants of MF6388.

In addition, compounds of the present invention may be prepared by fermentation of the culture MF6591, ATCC 74477.

The present invention also relates to the preparation of compounds of structural Formula I comprising:

(a) fermenting a culture of MF6591 (ATCC 74477), Ascochyta sp. or a mutant thereof to produce a fermentation broth, (b) extracting the fermentation broth with an organic solvent, (c) isolating the compounds of structural Formula I.

The compounds of structural Formula I are preferably isolated by partitioning the fermentation extract between the organic solvent and water, followed by size exclusion chromatography and normal or reverse-phase chromatography.

When any variable (e.g., $R^1$, $R^2$, etc.) occurs more than one time in any constituent or in Formula I, its definition on each occurrence is independent of its definition at every other occurrence. Also, combinations of substituents and/or variables are permissible only if such combinations result in stable compounds.

The compounds of the present inventions are useful in the inhibition of HIV integrase, the prevention or treatment of infection by human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by e.g., blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus, the compounds of this invention are commercial products to be sold for these purposes.

The present invention also provides for the use of a compound of structural Formula (I) to make a pharmaceutical composition useful for inhibiting HIV integrase and in the treatment of AIDS or ARC.

Applicants have discovered that compounds of structural Formula (I), are useful for inhibiting HIV integrase.

ATCC Deposit of MF6388 (ATCC 74478), identified as Sterile Fungus.

Before the U.S. filing date of the present application, a sample of MF6388 (ATCC 74478), Sterile Fungus, was deposited at the American Type Culture Collection (ATCC), 10801 University Boulevard, Manassas, Va. 20110-2209, United States of America, under the terms of the Budapest Treaty. The culture access designation is 74478. This deposit will be maintained in the ATCC for at least 30 years and will be made available to the public upon the grant of a patent disclosing it. It should be understood that the availability of a deposit does not constitute a license to practice the subject invention in derogation of patent rights granted by government action.
ATCC Deposit of MF6591 (ATCC 74477), identified as Ascochyta sp.

Before the U.S. filing date of the present application, a samnple of MF6388 (ATCC 74477), Ascochyta sp., was deposited at the American Type Culture Collection (ATCC), 10801 University Boulevard, Manassas, Va. 20110-2209, United States of America, under the terms of the Budapest Treaty. The culture access designation is 74477. This deposit will be maintained in the ATCC for at least 30 years and will be made available to the public upon the grant of a patent disclosing it. It should be understood that the availability of a deposit does not constitute a license to practice the subject invention in derogation of patent rights granted by government action.

General Characteristics and Descriptions of MF6388 (ATCC 74478), Sterile Fungus and MF6591 (ATCC 74477), Ascochyta sp.

In the following descriptions, MF6388 and MF6591 were edge inoculated with a 5 mm diameter plug on 2,100 mm petri dishes for each the following growth media. All cultures were incubated for 20 days at 25° C. and 67% relative humidity in 12 hr photoperiod in fluorescent light unless otherwise indicated. In addition, all capitalized color names are from Ridgway, Color Standards and Nomenclature, (Published by author, Washington D.C., 1912) 43p. +53.

Sterile Fungus (MF6388)

MF6388 was isolated from herbivore dung collected in New Mexico.

On oatmeal agar (Difco) culture mat attaining a diameter of 40 mm. Culture mat woolly from inoculation point to midway through the colony then thickly cottony until margin, grey-green (Pale Olive-Gray, Olive Gray), margin entire, white. Exudate forming as large, clear to light brown droplets near inoculation point and smaller, clear droplets closer to margin area. Reverse dark brown (Drab, Hair Brown). Soluble pigment absent.

On potato-dextrose agar (Difco), culture mat attaining a diameter of 64 mm. Culture mat densely cottony, more dense at the inoculation point than closer to the margin, white aerial mycelium over green (Sage Green, Slate Olive) mycelium, margin entire, white. Exudate forming as sparse, clear droplets. Soluble pigment dark red brown (Dark Indian Red, Indian Red).

On cornmeal agar (Difco), culture mat attaining a diameter of 75 mm (plate covered). Colony mat appressed, uncolored to slightly white. Margin entire, hyaline. Exudate, reverse and soluble pigment absent.

On YME agar (malt extract, 10.0 g; yeast extract, 4.0 g; dextrose, 4.0 g; agar, 20.0 g, distilled water, 1L) culture mat attaining a diameter of 66 mm. Culture mat woolly, forming dense tufts, tufts becoming smaller towards margin area, white throughout, margin entire, white. Exudate forming as medium sized, light brown to sparse (at margin), clear droplets. Soluble pigment dark red brown (Dark Indian Red, Indian Red). No growth at 37° C., in the dark and no humidity control.

Microscopic: Hyphae hyaline, branched, thin-walled, usually 2–4 µm wide. No sporulation observed.

Ascochyta sp. (MF6591)

MF6591 was isolated from *Urtica urens* collected in Ontigola, Aranjuez, Spain.

On oatmeal agar (Difco) colony mat attaining a diameter of 40 mm. Culture mat cottony, dissected, light gray (Pale Neutral Gray, Gull Gray), abundant black fruiting bodies oozing light pink near inoculation point. Margin entire, light brown. Reverse dark gray (Deep Purplish Gray, Purplish Gray). Soluble pigment and exudate absent.

On potato-dextrose agar (Difco), colony mat attaining a diameter of 33 mm. Culture mat cottony, consistent throughout, gray-green (Olive Gray, Light Olive-Gray, Deep Olive-Gray), sparse white aerial mycelium near inoculation point. Soluble pigment deep red-brown (Indian Red, Deep Indian Red). Reverse and exudate absent.

On cornmeal agar (Difco), colony mat attaining a diameter of 45 mm. Culture mat appressed, uncolored. Fruiting bodies black, clustered around inoculation plug in contact with agar, immature fruiting bodies scattered throughout culture mat, abundant near inoculation point. Reverse, soluble pigment and exudate absent.

On YME agar (malt extract, 10.0 g; yeast extract, 4.0 g; dextrose, 4.0 g; agar, 20.0 g, distilled water, 1L) attaining a diameter of 33 mm. Culture mat cottony to thick velvety, light orange to pink (Vinaceous Pink, Shell Pink), sections near inoculation point collapsed, blackish. Margin region very faint yellow-brown (Light Buff, Pale Ochraceous Buff), very edge of margin entire, uncolored, submerged. Soluble pigment dark red-brown to light red-brown (Chestnut Brown, Cinnamon-Rufous). Exudate and reverse absent. At 37° C., in the dark and no humidity control, no growth.

Microscopic: *Hyphae hyaline* to light brown, thin-walled, branched, septate, 4–5 µm wide. *Conidiomata pycnidial*, thin-walled, black, sphaerical, mostly immersed in agar, 150–200 µm, mature conidia oozes as a pink mass from ostiole. Conidiogenous cells phialidic, 1-celled, hyaline, 5–10×4–5 µm. Conidia, hyaline, cylindrical, 1 medially septate, thin-walled, 10–15×3–4 µm.

In general, MF6388 (ATCC 74478) is a strain cultured on a solid medium, or in an aqueous nutrient medium containing sources of assimilable carbon and nitrogen. For example, the cultures may be grown under submerged aerobic conditions (e.g., shaking culture, submerged culture, etc.)

In general, MF6591 (ATCC 74477) is strain that may be cultured on a solid medium, or in an aqueous nutrient medium containing sources of assimilable carbon and nitrogen. For example, the cultures may be grown under submerged aerobic conditions (e.g., shaking culture, submerged culture, etc.)

The sources of carbon in the nutrient medium are carbohydrates such as glucose, xylose, galactose, glycerin, starch, sucrose, dextrin, and the like. Other sources which may be included are maltose, rhamnose, raffinose, arabinose, mannose, sodium succinate, and the like.

The sources of nitrogen are yeast extract, meat extract, peptone, gluten meal, cottonseed meal, soybean meal and other vegetable meals (partially or totally defatted), casein hydrolysates, soybean hydrolysates, and yeast hydrolysates, corn steep liquor, dried yeast, wheat germ, feather meal, peanut powder, distiller's solubles, etc., as well as inorganic and organic nitrogen compounds such as ammonium salts (e.g., ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

Agitation and aeration of the culture mixture may be accomplished in a variety of ways. Agitation may be provided by a propeller or similar mechanical agitation equipment, by revolving or shaking the fermentor, by various pumping equipment, or by the passage of sterile air through the medium. Aeration may be effected by passing sterile air through the fermentation mixture.

The fermentation is usually conducted at a temperature between about 20° C. and 30° C., preferably 22–25° C., for a period of about 14–21 days, which may be varied according to fermentation conditions and scales.

Preferred culturing/production media for carrying out the fermentation those set forth in the Examples.

As to the conditions for the production of cells in massive amounts, submerged aerobic cultural conditions is one method of culturing the cells. For the production in small amounts, a shaking or surface culture in a flask or bottle is employed. The use of fermentors (tanks) is preferred for the generation of large quantities of materials. Fermentors can be sterilized with the production medium or can be sterilized empty and the medium sent through a continuous sterilizer, which is preferred for very large fermentations (20,000 gallons or larger). Preferably, the pH of the medium is adjusted to about 6–7, generally using acid or base additions, preferably made automatically with a pH electrode and a controller. The parameters for fermenter operation include agitation, aeration, temperature and pressure. Agitation is preferably carried out by mixing the medium with a number of impellers mounted on a rotating agitator shaft located in the midst of the tank. Aeration may be carried out by a variety of means, preferably by bubbling sterile air into the medium (subsurface sparging). The tank is preferably maintained under positive pressure. Temperature is preferably maintained at between about 20° C. and 30° C.

When the growth is carried out in large tanks, vegetative forms of the organism for inoculation in the production tanks may be employed in order to avoid growth lag in the process of production. This requires production of a vegetative inoculum of the organism by inoculating a relatively small quantity of culture medium with spores or mycelia of the organism produced in a "slant" and culturing said inoculated medium, also called the "seed medium", and then transferring the cultured vegetative inoculum aseptically to large tanks. The fermentation medium, in which the inoculum is produced, is generally sterilized prior to inoculation. The pH of the medium is generally adjusted to about 6–7 prior to the autoclaving step, generally using acid or base additions, preferably made automatically with a pH electrode and a controller.

Preferred culturing/production media for carrying out the fermentation are those set forth in the Examples.

After growth is completed, the cells harvested by adding the appropriate solvent, e.g., methylethylketone, to the entire culture medium and cells. If the culture is grown in a liquid fermentation, the growth could be harvested by other conventional methods, e.g., centrifugation and filtration, and then extracted with the appropriate solvent, e.g., methylethylketone.

The product of the present invention can be recovered from the culture medium by conventional means which are commonly used for the recovery of other known substances. The substances produced may be found in either or both the cultured mycelium and broth filtrate, and accordingly can be isolated and purified from the mycelium and the filtrate, which are obtained by filtering or centrifuging the cultured broth, by a conventional method such as concentration under reduced pressure, lyophilization, extraction with a conventional solvent, such as methylene chloride or methanol and the like, pH adjustment, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), crystallization, recrystallization, and the like. A preferred method is extraction of cultured whole broth with methylethylketone, followed by filtration of the extract through filtering aid such as diatomaceous earth. The methylethylketone layer of the filtrate is separated and concentrated to dryness initially by evaporating under reduced pressure followed by lyophilization. The compounds are finally isolated either by solvent partitioning, crystallization, gel filtration or by preparative HPLC on reversed phase systems.

Compounds of Formula (I) may be isolated from the aerobic fermentation of a culture of ME6388 (ATCC 74478). A culture of MF6388 (ATCC 74478) is defined as substantially free of its natural soil contaminants and capable of forming compounds of structural Formula (I) in recoverable amounts. The culture employed in the present invention should be free from viable contaminating microorganisms deleterious to the production of the compound of structural Formula (I). A biologically pure culture of MF6388 (ATCC 74478) may also be employed.

Compounds of Formula (I) may be isolated from the aerobic fermentation of a culture of MF6591 (ATCC 74477). A culture of MF6591 (ATCC 74477) is defined as substantially free of its natural soil contaminants and capable of forming compounds of structural Formula (I) in recoverable amounts. The culture employed in the present invention should be free from viable contaminating microorganisms deleterious to the production of the compound of structural Formula (I). A biologically pure culture of MF6591 (ATCC 74477) may also be employed.

The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, omithine, choline, N,N'-dibenzylethylenediamine, chloroprocaine, diethanolamine, procaine, N-benzylphenethylamine, diethylamine, piperazine, tris (hydroxymethyl)aminomethane, and tetramethylammonium hydroxide. These salts may be prepared by standard procedures, e.g. by reacting a free acid with a suitable organic or inorganic base. Where a basic group is present, such as amino, an acidic salt, i.e. hydrochloride, hydrobromide, acetate, pamoate, and the like, can be used as the dosage form.

Also, in the case of an acid (—COOH) or alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

The terms "administration of" and or "administering a" compound should be understood to mean providing a compound of the invention or a prodrug of a compound of the invention to the individual in need of treatment.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically-effective amount of a compound of the present invention.

As used herein, the term "composition" is intended to encompass a product comprising the specified ingredients in the specified amounts, as well as any product which results directly, or indirectly, from combination of the specified ingredients in the specified amounts.

By "pharmaceutically acceptable" it is meant the carrier, diluent or excipient must be compatible with the other ingredients of the formulation and not deleterious to the recipient thereof.

These pharmaceutical compositions may be in the form of orally-administrable suspensions or tablets, nasal sprays, sterile injectible preparations, for example, as sterile injectible aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectible solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-initiating excipient, such as cocoa butter, synthetic glyceride esters of polyethylene glycols, which are solid at ordinary temperatures, but liquefy and/or dissolve in the rectal cavity to release the drug.

The compounds of this invention can be administered orally to humans in a dosage range of 1 to 1000 mg/kg body weight in divided doses. One preferred dosage range is 0.1 to 200 mg/kg body weight orally in divided doses. Another preferred dosage range is 0.5 to 100 mg/kg body weight orally in divided doses. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV integrase inhibitor compounds with one or more agents useful in the treatment of AIDS. For example, the compounds of this invention may be effectively administered, whether at periods of pre-exposure and/or post-exposure, in combination with effective amounts of the AIDS antivirals, imunomodulators, antiinfectives, or vaccines, such as those in the following table.

| Drug Name | Manufacturer | Indication |
|---|---|---|
| ANTIVIRALS | | |
| 097 | Hoechst/Bayer | HIV infection, AIDS, ARC (non-nucleoside reverse transcriptase inhibitor) |
| Amprenavir 141 W94 GW 141 | Glaxo Wellcome | HIV infection, AIDS, ARC (protease inhibitor) |
| Abacavir GW 1592 1592U89 | Glaxo Welcome | HIV infection, AIDS, ARC (reverse transcriptase inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in |

-continued

| Drug Name | Manufacturer | Indication |
|---|---|---|
| Ansamycin LM 427 | Adria Laboratories (Dublin, OH) Erbamont (Stamford, CT) | combination w/Retrovir ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (protease inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| EL10 | Elan Corp, PLC (Gainesville, GA) | HIV infection |
| Efavirenz (DMP 266) (−)6-Chloro-4(S)-cyclopropylethynyl-4(S)-trifluoro-methyl-1,4-dihydro-2H-3,1-benzoxazin-2-one, | DuPont (SUSTIVA ®), Merck (STOCRIN ®) | HIV infection, AIDS, ARC (non-nucleoside RT inhibitor) |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| Compound Q | Merck | HIV infection, AIDS, ARC, asymptomatic HIV positive CMV retinitis |
| ISIS 2922 | ISIS Pharmaceuticals | HIV-assoc. diseases |
| KNI-272 | Nat'l Cancer Institute | HIV infection, AIDS, ARC (reverse transcriptase inhibitor); also with AZT |
| Lamivudine, 3TC | Glaxo Wellcome | |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (protease inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma, in combination with other therapies |
| ABT-378 | Abbott | HIV infection, AIDS, ARC (protease inhibitor) |
| JE2147/AG1776 | Agouron | HIV infection, AIDS, ARC (protease inhibitor) |
| T-20 T-1249 | Trimeris | HIV infection, AIDS, ARC (fusion inhibitor) |
| BMS 232632 | Bristol-Myers-Squibb | HIV infection, AIDS, ARC (protease inhibitor) |
| IMMUNO-MODULATORS | | |
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | blocks HIV fusion with CD4 + cells |
| Gamma Interferon | Genentech | ARC, in combination w/TNF (tumor necrosis factor) |
| Granulocyte Macrophage Colony Stimulating | Genetics Institute Sandoz | AIDS |

-continued

| Drug Name | Manufacturer | Indication |
|---|---|---|
| Factor Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute | HIV infection |
| Tumor Necrosis Factor; TNF | Genentech | ARC, in combination w/gamma Interferon |
| etanercept | Immunex Corp (Enbrel ®) | rheumatoid arthritis |
| infliximab | Centocor (Remicade ®) | rheumatoid arthritis and Crohn's disease |
| ANTI-INFECTIVES | | |
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |
| Intraconazole-R51211 | Janssen Pharm. | histoplasmosis; cryptococcal meningitis |
| Trimetrexate | Warner-Lambert | PCP |
| OTHER | | |
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |
| Total Enteral Nutrition | Norwich Eaton Pharmaceuticals | diarrhea and malabsorption related to AIDS |

It will be understood that the scope of combinations of the compounds of this invention with HIV/AIDS antivirals, immunomodulators, anti-infectives or vaccines is not limited to the list in Table 1 above, but includes in principle any combination with any pharmaceutical composition useful for the treatment of AIDS.

One preferred combination is a compound of the present invention and a nucleoside inhibitor of HIV reverse transcriptase such as AZT, 3TC, ddC, or ddI. Another preferred combination is a compound of the present invention and a non-nucleoside inhibitor of HIV reverse transcriptase, such as efavirenz, and optionally a nucleoside inhibitor of HIV reverse transcriptase, such as AZT, 3TC, ddC or ddI. Still another preferred combination is any one of the foregoing combinations further comprising an additional HIV protease inhibitor such as indinavir, Compound Q, nelfinavir, ritonavir, saquinavir, amprenavir, or abacavir. A preferred additional inhibitor of HIV protease is the sulfate salt of indinavir. Other preferred additional protease inhibitors are nelfinavir and ritonavir. Still another preferred additional inhibitor of HIV protease is saquinavir which is administered in a dosage of 600 or 1200 mg tid.

Other preferred combinations include a compound of the present invention with the following (1) efavirenz, optionally with AZT and/or 3TC and/or ddI and/or ddC, and optionally with indinavir; (2) any of AZT and/or ddI and/or ddC and/or 3TC, and optionally with indinavir; (3) d4T and 3TC and/or AZT; (4) AZT and 3TC; and (5) AZT and d4T.

In such combinations the compound of the present invention and other active agents may be administered together or separately. In addition, the administration of one agent may be prior to, concurrent to, or subsequent to the administration of other agent(s). These combinations may have unexpected effects on limiting the spread and degree of infection of HIV.

Efavirenz is (−)-6-chloro-4-cyclopropylethynyl-4-trifluoromethyl-1,4-dihydro-2H-3,1-benzoxazin-2-one, also known as DMP-266 or SUSTIVA® (DuPont) or STOCRIN® (Merck). Efavirenz and its utility as an HIV reverse transcriptase inhibitor is described in U.S. Pat. No. 5,519, 021 and in the corresponding PCT published application, WO 95/20389. Efavirenz can be synthesized by the protocol of U.S. Pat. No. 5,633,405. Additionally, the asymmetric synthesis of an enantiomeric benzoxazinone by a highly enantioselective acetylide addition and cyclization sequence is described in Thompson et al., well as in the PCT publication, WO 96/37457.

AZT is 3'-azido-3'-deoxythymidine, is also known as zidovudine, and is available from Burroughs-Wellcome under the tradename RETROVIR®. Stavudine is 2',3'-didehydro-3'-deoxythymidine, is also known as 2',3'-dihydro-3'-deoxythymidine and d4T, and is available from Bristol-Myers Squibb under the tradename ZERIT®. 3TC is (2R-cis)-4-Amino-1-[2-(hydroxymethyl)-1,3-oxathiolan-5-yl]-2(1H)-pyrimidinone, is also known as (−)-1-[(2R,5S)-2-(hydroxymethyl)-1,3-oxathiolan-5-yl]cytosine and lamivudine, and is available from Glaxo Wellcome under the tradename EPIVIR®. ddC is 2',3'-dideoxycytidine, is also known as zalcitabine, and is available from Hoffman LaRoche under the tradename HIVID®. ddI is 2',3'-dideoxyinosine, is also known as didanosine, and is available from Bristol-Myers-Squibb under the tradename VIDEX®. The preparation of ddC, ddI and AZT are also described in EPO 0,484,071.

Indinavir is N-(2(R)-hydroxy-1(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide, and can be prepared as described in U.S. Pat. No. 5,413,999. Indinavir is generally administered as the sulfate salt at a dosage of 800 mg three times a day. Indinavir is available from Merck under the tradename CRIXIVAN®.

Compound Q is N-(2(R)-hydroxy-1(S)-indanyl)-2(R)-phenylmethyl-4(S)-hydroxy-5-(1-(4-(2-benzo[b]furanylmethyl)-2(S)-N'-(t-butylcarboxamido)-piperazinyl)) pentaneamide, preferably administered as the sulfate salt. Compound Q can be prepared as described in U.S. Pat. No. 5,646,148.

Ritonavir is [5S-(5R*,8R*,10R*, 11R*)]]-10-hydroxy-2-methyl-5-(1-methylethyl)-1-[2-(1-methylethyl)-4-thiazolyl]-3,6-dioxo-8,11 -bis(phenylmethyl)-2, 4, 7, 12-tetraazatridecan-13-oic acid 5-thiazolylmethyl ester, also known as 5-thiazolylmethyl [(aS)-a-[(1S,3S)-1-hydroxy-3-[(2S)-2-[3-[(2-isopropyl-4-thiazolyl)methyl]-3-methylureido]-3-methylbutyramido]-4-phenylbutyl] phenethyl]carbamate. It is available from Abbott under the tradename NORVIR®. Ritonavir can be prepared as described in U.S. Pat. No. 5,484,801.

Nelfinavir is [3S-[2(2S*,3S*),3a,4ab,8ab]]-N-(1,1-dimethylethyl)decahydro-2-[2-hydroxy-3-[(3-hydroxy-2-methylbenzoyl)amino]-4-(phenylthio)butyl]-3-isoquinolinecarboxamide monomethanesulfonate, also known as (3S,4aS,8aS)-N-tert-Butyl-2-[(2R,3R)-3-(3,2-crestoamido)-2-hydroxy-4-(phenylthio)butyl]decahydro-3-isoquinolinecarboxamide monomethanesulfonate and VIRACEPT®, which is commerically available from Agouron. Nelfinavir can be prepared as described in U.S. Pat. No. 5,484,926.

Saquinavir is N-tert-butyl-decahydro-2-[2(R)-hydroxy-4-phenyl-3(S)-[[N-(2-quinolylcarbonyl)-L-asparaginyl] amino]butyl]-(4aS,8aS)-isoquinoline-3(S)-carboxamide, also known as INVIRASE®. Saquinavir can be prepared in accordance with procedures disclosed in U.S. Pat. No. 5,196,438. INVIRASE® (saquinavir mesylate) is available from Roche Laboratories. Saquinavir can be prepared as described in U.S. Pat. No. 5,196,438.

Amprenavir is 4-amino-N-((2 syn,3S)-2-hydroxy4-phenyl-3-((S)-tetrahydrofuran-3-yloxycarbonylamino)- butyl)-N-isobutyl-benzenesulfonamide, also known as Compound 168 and 141 W94. Amprenavir is an aspartyl protease inhibitor that can be prepared by following the procedures described in U.S. Pat. No. 5,585,397. Amprenavir is available under the tradename AGENERASE® from Glaxo Wellcome. Amprenavir can be prepared as described in U.S. Pat. No. 5,783,701.

Abacavir is (1S,4R)-cis-4-[2-amino-6-(cyclopropylamino)-9H-purin-9-yl]-2-cyclopentene-1-methanol, also known as 1592U89. Abacavir can be prepared by following the protocol of EP 0434450. The following examples are provided to further illustrate details for the preparation and use of the compounds of the present invention. The examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds. All temperatures are in degrees Celsius unless noted otherwise.

Abbreviations: DMF is dimethyl formamide; ESIMS represents Electron Spray Ionization Mass Spectroscopy; Et represents ethyl; HPLC is high pressure liquid chromatography; HREIMS respresents High Resolution Electron Impact Mass Spectroscopy; IPA is isopropyl alcohol; MEK is methyl ethyl ketone; Me represent methyl; rh represents relative humidity, TFA is trifluoroacetic acid; THF is tetrahydrofuran; TLC is thin layer ($SiO_2$) chromatography.

EXAMPLE 1

Fermentation of MF6388 (ATCC 74478) Sterile Fungus

A. Media
SEED MEDIUM:

| Component | g/L |
|---|---|
| Yeast extract | 4.0 |
| Malt extract | 8.0 |
| Glucose | 4.0 |
| Junlon | 1.5 |

The medium was prepared with distilled water, the pH adjusted to 7.0 prior to sterilization, and was dispensed at 50 mL/250 mL unbaffled Erlenmeyer flask. Cotton closures were used. Sterilization was at 121° C. for 20 minutes.
PRODUCTION MEDIUM:
1. Solid portion:
   675 cc vermiculite was added to a 2 liter roller bottle which was plugged with latex closure and autoclaved for 60 minutes, plus 30 minutes and dried.
2. Liquid portion

| Component | Amount |
|---|---|
| Glucose | 150.0 g/L |
| Fructose | 15.0 g/L |
| Sucrose | 40.0 g/L |
| Casamino acids | 2.0 g/L |

-continued

| Component | Amount |
|---|---|
| Asparagine | 2.0 g/L |
| Yeast extract | 1.0 g/L |
| $Na_2HPO_4$ | 0.5 g/L |
| $MgSO_4.7H_2O$ | 1.0 g/L |
| $CaCl_2$ | 0.5 g/L |
| K-elements | 1.0 mL/L |
| pH to 7.0 | |

The medium was prepared with distilled water, dispensed at 220 mL in 500 mL bottles and sterilized at 121° C. for 20 minutes.

| K-elements | |
|---|---|
| Component | Amount |
| $FeCl_3.6H_2O$ | 5.8 g/L |
| $MnSO_4.H_2O$ | 0.1 g/L |
| $CoCl_2.6H_2O$ | 0.02 g/L |
| $CuSO_4.5H_2O$ | 0.015 g/L |
| $NaMoO_4.2H_2O$ | 0.012 g/L |
| $ZnCl_2$ | 0.02 g/L |
| $SnCl_2.2H_2O$ | 0.005 g/L |
| $H_3BO_3$ | 0.01 g/L |
| KCl | 0.02 g/L |
| HCl (concentrated) | 2.0 mL/L |

B. Inoculum Preparation

An agar slant was used to prepare FVMs (frozen vegetative mycelia). A portion of the agar slant was transferred aseptically to seed medium. (The composition of the seed medium is detailed above). The flasks were incubated on a 2-inch throw gyratory shaker, 220 rpm for 7 days at 25° C, 85% relative humidity (rh), to obtain biomass. Portions of the biomass were transferred into sterile vials containing glycerol and frozen (as FVM). These were maintained in a final concentration of 10–15% glycerol at −75° C.

C. Seed Culture

Frozen vials (FVM) were thawed to room temperature and used to inoculate seed cultures, at 1.0 mL per 50 mL seed medium. The cultures were grown on a gyratory shaker (220 rpm) for 4 days at 25° C., 85% rh, until a sufficient amount of biomass was obtained.

D. Production

The composition of the solid substrate fermentation medium is shown above. An aliquot (12 mL) of each grown seed was placed into 220 mL of the liquid portion of the production. This was swirled vigorously to disperse the biomass. The contents were dispensed by pouring into a 2-liter roller culture vessel which contained 675 cubic centimeters of steam-sterilized large-particle vermiculite. The contents of the roller bottle were shaken/mixed to insure homogeneous inoculation and coverage. The roller bottles were incubated horizontially, revolving at approximately 4 rpm on a Wheaton roller apparatus at 22° C., 75% rh for 20 days, to obtain secondary metabolite production in the fermentation medium. The contents of each roller bottle were extracted with 200–250 mnL methyl ethyl ketone and the solids discarded.

EXAMPLE 2

Fermentation of MF6591 (ATCC 74477) Ascochyta sp

A. Media:

Seed medium contained the following in g/L: corn steep liquor, 5 g; tomato paste, 40; oat flour, 10; glucose, 10; agar, 4; $FeSO_4·7H_2O$, 0.01; $MnSO_4·4H_2O$, 0.01; $CuCl_2·2H_2O$, 0.00025; $CaCl_2$, 0.001; $H_3BO_3$, 0.00056; $(NH_4)_6Mo_7O_{24}·4H_2O$, 0.00019; $ZnSO_4·7H_2O$, 0.002. The pH was adjusted to 6.8.

Production media contained the following per 250 mL flask: brown rice, 10 g; base liquid, 20 mL. Base liquid contained the following in g(L: yeast extract, 1; sodium tartrate, 0.5; $KH_2PO_4$, 0.5. The flasks were autoclaved for 15 minutes at 121° C, 15 psi and stored. Prior to innoculation, 15 mL of distilled water were added per flask and the flasks were sterilized for 20 minutes at 121° C., 15 psi.

B. Inoculum Preparation

Frozen vegetative mycelia (FVM) were prepared by inoculating 50 mL of seed medium in a 250 mL flask and incubating at 25° C., 85% relative humidity and at 200 rpm for 3–5 days. Aliquots of the culture were frozen and used as a source of inoculum for future experiments.

C. Seed Culture

To 50 mL of seed media in a 250 mL flask, 2.0 mL of FVM was added as inoculum and the flasks were incubated at 25° C., 85% relative humidity and at 200 rpm for days 2–3 days.

D. Production of Culture and Extraction

To 50 mL of production media in a 250 mL flask, 1 mL of seed culture was added as inoculum and the flasks were incubated at 25° C., 85% relative humidity for 24 days. Each flask was then extracted with 50 mL of methyl ethyl ketone and the solids were discarded.

EXAMPLE 3

Isolation of Compounds A and B from MF6591:

The fungus was grown on a brown rice based liquid medium for 31 days and 1.4 L of the broth was extracted with 1.2 volumes of methyl ethyl ketone (MEK). The layers were separated to give 1.4 L MEK extract. The extract was concentrated under reduced pressure to give an aqueous solution that was diluted by addition of 300 mL of water and 50 mL of methanol. This methanolic aqueous solution was partitioned three times with one volume each of hexane followed by five times with one volume each of ethyl acetate. All of the integrase activity was concentrated in ethyl acetate extract. This extract was concentrated to dryness to give a brown gum. Five grams of this material was chromatographed on a 2.0 L SEPHADEX LH20 column. Elution of the column with methanol eluted the activity in a broad zone from 0.6 L to 1.7 L column volume. The most active fraction contained mostly the mixture of Compounds A and B. An aliquot of this fraction was chromatographed on a reverse phase HPLC using ZORBAX RX C-8 (22×250 mm) column. The column was eluted at 8 mL/min with a gradient of acetonitrile in water containing 0.05% trifluoroacetic acid. The gradient started with 20% acetonitrile to 40% acetonitrile in 50 minutes, held at 40% for 10 minutes and then the acetonitrile concentration was increased to 100% over 20 minutes. Lyophilization of fractions eluting in between 31–35 and 52–59 minutes gave Compounds B and A, respectively, as brown powders. Compound B: $UV\lambda_{max}$: 210, 230, 315 nm. ESIMS (m/z) 405 (M+H)$^+$, 403 (M−H)−; HREIMS (m/z): 404.1110 (M$^+$, calcd for $C_{20}H_{20}O_9$:

404.1107), 209.0436 (calcd for $C_{10}H_9O_5$: 209.0450), 195.0623 (calcd for $C_{10}H_{11}O_4$: 195.0657); for $^1H$ and $^{13}C$ NMR see Table 1. Compound A: UV$\lambda_{max}$: 215, 235, 320 nm. ESIMS (m/z) 403 (M+H)$^+$, 401 (M—H)-; HREIMS (m/z): 402.0960 (M$^+$, calcd for $C_{20}H_{18}O_9$: 402.0950), 209.0452 (calcd for $C_{10}H_9O_5$: 209.0450), 194.0576 (calcd for $C_{10}H_{11}O_4$: 194.0579); for $^1H$ and $^{13}C$ NMR see Table 1.

EXAMPLE 4

Isolation of Compound A from MF6388:

Sixty mL methyl ethyl ketone extract of MF6388 grown on vermiculite solid medium was concentrated to dryness to give a brown gum. This material was dissolved in a 1:1 mixture of methylene chloride and methanol and chromatographed on a 1.0 L column of SEPHADEX LH20. The column was eluted with methanol. A single combined active fraction was chromatographed on a ZORBAX RX C-8 reverse phase HPLC column. Gradient elution with 20 to 80% acetonitrile in water containing 0.05% TFA over 40 minutes at a flow rate of 8 mL/min gave after lyophilization Compound A as a brown powder.

TABLE 1

1H NMR and 13C NMR spectral data of Compounds B and A

Compound B; R = CH$_2$OH
Compound A; R = CHO

| Position | δC Compound B CD$_3$CN | δH Compound B CD$_3$CN | δC Compound A CDCl$_3$ + CD$_3$CN | δH Compound A CDCl$_3$ + CD$_3$CN |
| --- | --- | --- | --- | --- |
| 2 | 97.8 | | 97.8 | |
| 3 | 121.3 | | 120.7 | |
| 4 | 140.1* | | 140.1* | |
| 5 | 140.4 | | 142.2 | |
| 6 | 148.6 | | 148.7 | |
| 7 | 101.4 | 7.03, s | 101.8 | 7.06, s |
| 8 | 121.1 | | 120.4 | |
| 9 | 193.8 | | 193.7 | |
| 10 | 77.4 | | 77.1 | |
| 11 | 114.1 | | 121.3 | |
| 12 | 130.5 | | 126.0 | |
| 13 | 107.3 | 6.70, s | 105.7 | 7.14, s |
| 14 | 147.7 | | 147.8 | |
| 15 | 134.4 | | 140.9 | |
| 16 | 142.0* | | 140.8* | |
| 18 | 26.4 | 2.09, s | 26.5 | 2.15, s |
| 19 | 22.2 | 1.76, s | 25.8 | 1.87, s |
| 20 | 60.9 | 4.58, d, 12.8 4.40, d, 12.8 | 190.6 | 10.21, s |
| 21 | 56.4 | 3.75, s | 56.6 | 3.75, s |
| 22 | 56.6 | 3.83, s | 56.7 | 3.85, s |

EXAMPLE 5

HIV Integrase Assay: Strand Transfer Catalyzed by Recombinant Integrase

Assays for the strand transfer activity of integrase were conducted according to Wolfe, A. L. et al., J. Virol. 70, 1424 (1996), hereby incorporated by reference for these purposes. Representative compounds tested in the integrase assay demonstrated IC50's less than 10 micromolar.

EXAMPLE 6

Oral Composition

As a specific embodiment of an oral composition of a compound of this invention, 50 mg of a compound of the present invention is formatted with sufficient finely divided lactose to provide a total amount of 580 to 590 mg to fill a size 0 hard gelatin capsule.

While the foregoing specification teaches the principles of the present invention, with examples provided for the purpose of illustration, it will be understood that the practice of the invention encompasses all of the usual variations, adoptions, or modifications, as come within the scope of the following claims and their equivalents.

What is claimed:

1. A compound of Formula I:

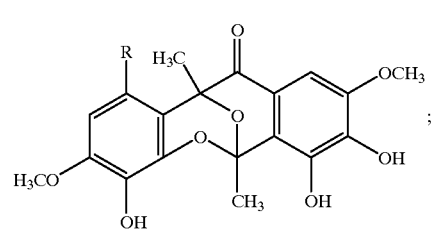

(I)

wherein:
R is selected from:
(a) —CH$_2$OH, and
(b) —CH(=O);
or a pharmaceutically acceptable salt thereof.

2. The compound according to claim 1, which is:

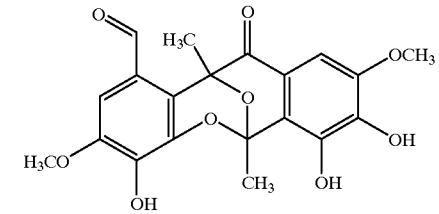

or a pharmaceutically acceptable salt thereof.

3. The compound according to claim 1, which is:

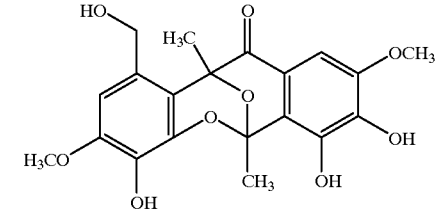

or a pharmaceutically acceptable salt thereof.

4. A pharmaceutical composition comprising an effective amount of a compound according to claim 1, or a pharmaceutically acceptable salt thereof, and a pharmaceutically acceptable carrier.

5. A pharmaceutical composition comprising a therapeutically effective amount of a compound of claim 1, or a pharmaceutically acceptable salt thereof, in combination with a therapeutically effective amount of an AIDS treatment agent selected from:

(a) an AIDS antiviral agent, (b) an immunomodulator, and (c) an anti-infective agent.

6. The pharmaceutical composition according to claim 5 wherein the AIDS antiviral agent is N-(2(R)-hydroxy-1(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide, or a pharmaceutically acceptable salt thereof.

7. A pharmaceutical composition made by combining the compound of claim 1, or a pharmaceutically acceptable salt thereof, and a pharmaceutically acceptable carrier.

8. A process for making a pharmaceutical composition comprising combining a compound of claim 1, or a pharmaceutically acceptable salt thereof, and a pharmaceutically acceptable carrier.

9. A method of inhibiting HIV integrase, comprising the administration to a mammal in need of such treatment a therapeutically effective amount of a compound of claim 1, or a pharmaceutically acceptable salt thereof.

10. A method of treating infection by HIV, or of treating AIDS or ARC, comprising the administration to a mammal in need of such treatment a therapeutically effective amount of a compound of claim 1, or a pharmaceutically acceptable salt thereof.

11. The method according to claim 10 additionally comprising the administration of a therapeutically effective amount of another AIDS treatment agent selected from:

(a) an AIDS antiviral agent, (b) an immunomodulator, and (c) an anti-infective agent.

12. The method according to claim 11 wherein the AIDS antiviral agent is N-(2(R)-hydroxy-1(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide, or a pharmaceutically acceptable salt thereof.

* * * * *